United States Patent

Krüger et al.

[11] Patent Number: 5,313,003
[45] Date of Patent: May 17, 1994

[54] COPOLYMERIZABLE FLUORINATED COMPOUNDS, A PROCESS FOR THEIR PREPARATION AND THERMOPLASTIC FLUOROPOLYMERS OBTAINABLE THEREFROM

[75] Inventors: Ralf Krüger, Bergisch Gladbach; Michael Negele, Solingen; Albrecht Marhold, Leverkusen, all of Fed. Rep. of Germany

[73] Assignee: Bayer Aktiengesellschaft, Leverkusen, Fed. Rep. of Germany

[21] Appl. No.: 75,207

[22] Filed: Jun. 10, 1993

[30] Foreign Application Priority Data

Jun. 17, 1992 [DE] Fed. Rep. of Germany ....... 4219764

[51] Int. Cl.$^5$ ............... C07C 43/192; C07C 43/17
[52] U.S. Cl. ........................... 568/669; 568/685; 526/247
[58] Field of Search ................. 568/669, 685

[56] References Cited

U.S. PATENT DOCUMENTS

| | | |
|---|---|---|
| 2,244,325 | 6/1941 | Bird . |
| 2,574,902 | 11/1951 | Bechtold et al. . |
| 2,917,548 | 12/1959 | Dixon . |
| 3,250,808 | 5/1966 | Moore, Jr. et al. . |
| 3,440,175 | 4/1969 | Weldes et al. . |
| 3,440,176 | 4/1969 | Sippel . |
| 3,462,374 | 8/1969 | Klosak . |
| 3,655,765 | 4/1972 | Gelfand . |
| 3,673,104 | 6/1972 | Albrecht . |
| 3,947,376 | 3/1976 | Albrecht . |

FOREIGN PATENT DOCUMENTS

| | | |
|---|---|---|
| 303298 | 2/1989 | European Pat. Off. . |
| 1143845 | 6/1989 | Japan ................................. 568/685 |
| 1348705 | 3/1974 | United Kingdom . |

OTHER PUBLICATIONS

D. K. Iler, "The Chemistry of Silca", Wiley, New York, (1979).
G. W. Sears, Jr., "Determination of Specific Surface . . . Sodium Hydroxide", Analytical Chemistry, vol. 28, No. 12, Dec. 1956.
C. G. Krespan, "Negative Substituents in the Claisen Rearrangement", Tetrahedron, vol. 23, pp. 4243–4249, Pergamon Press Ltd., (1967).

Primary Examiner—Marianne M. Cintins
Assistant Examiner—Rebecca Cook
Attorney, Agent, or Firm—Sprung Horn Kramer & Woods

[57] ABSTRACT

A 2-allyl-perfluoroalkyl-trifluorovinyl ether of the formula

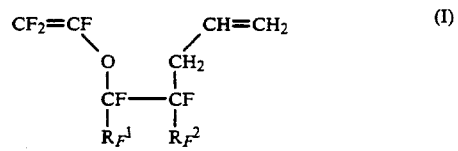

wherein
$R^1_F$ and $R^2_F$ represent either —$CF_3$ or, together, $(CF_2)_n$ where n=2 or 3.

2 Claims, No Drawings

COPOLYMERIZABLE FLUORINATED COMPOUNDS, A PROCESS FOR THEIR PREPARATION AND THERMOPLASTIC FLUOROPOLYMERS OBTAINABLE THEREFROM

The present invention relates to 2-alkyl-perfluoro-(cyclo)alkyl-trifluorovinyl ethers, a process for their preparation and homo- and copolymers prepared therefrom.

The monomers according to the invention may be polymerized by radical polymerization with the formation of ring structures in the polymer chain (cyclopolymerization).

The polymers produce amorphous, transparent coatings or molded items with glass transition temperatures between 60° and 150° C. and have good solubility characteristics in a number of organic solvents. The latter has proven to be particularly advantageous in that application onto a surface to be coated is just as easy as is subsequent dissolution, so that the ability to recycle materials coated with the fluoropolymers according to the invention is increased.

When coating other polymeric materials, e.g. in the form of optical fibers, with fluoropolymers, there is frequently the problem that, due to the lack of solubility and relatively high fusion or softening temperature of fluoropolymers, application has to take place at too high a temperature for the material concerned, so that as a rule thermal stability and/or heat resistance are lost under the extreme conditions.

Amorphous, highly transparent fluoropolymers with cyclic chain-structural elements are known, e.g. from U.S. Pat. No. 4,975,505. However, these polymers have too high a glass transition temperature, at least 150° C., for many applications and, furthermore, satisfactory solubility characteristics are only demonstrated in selected fluorinated compounds.

EP-A 303,292 describes amorphous fluoropolymers which may be obtained by cyclopolymerization, which merely have glass transition temperatures of less than 100° C. and which are likewise not soluble in common organic solvents.

The present invention provides 2-allyl-perfluoroalkyl trifluorovinyl ethers of the following formula (1)

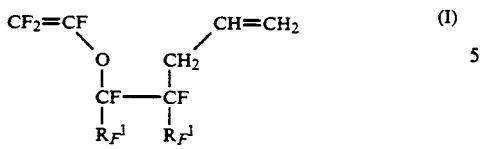

wherein $R^1_F$ and $R^2_F$ represent either —$CF_3$ or, together, $(CF_2)_n$ where n=2 or 3.

Monomers of the formula (1) where n=3 are preferred.

During radical polymerization, chain structures with the following structural units are produced:

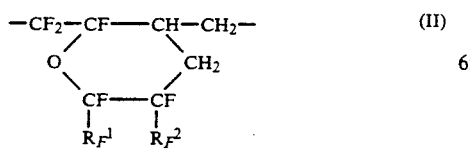

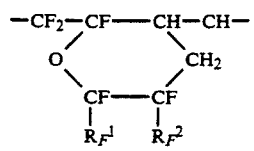

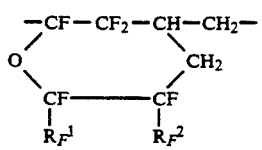

Degrees of polymerization are achieved, depending on the temperature of polymerization, which correspond to a residual content of C—C double bonds of less than 10% to 2% of the number of double bonds in the monomer.

The process according to the invention for preparing the monomers according to the invention is characterized in that a) appropriate 2-allyl-substituted perfluorocycloketones or perfluoroketones are reacted with hexafluoropropene oxide, b) the 2-(allylperfluorocycloalkoxy)- or 2-(allylperfluoroalkoxy)-perfluoropropanoic acid fluorides obtained are converted into their sodium salts by alkaline saponification and c) the sodium salts are decarboxylated at 150°–350° C.

To reduce the production of 2-allyl-perfluoroalkyl-1,1,1,2-tetrafluoroethyl ethers as a side product, the sodium salts obtained under b) are prefer-ably dissolved in aromatic hydrocarbons, insoluble salts are separated from the solution and the sodium salts are dried azeotropically.

The 2-alkyl-substituted perfluorocycloketones or perfluoroketones required to prepare the monomers according to the invention are known per se; see e.g. Tetrahedron 23 4243 (1967); U.S. Pat. No. 3,655,765.

However, it was extremely surprising that reaction of these starting compounds with hexafluoropropene oxide is possible with satisfactory yields, despite steric hindrance of the carbonyl group by the 2-allyl substituents.

According to the invention, the reaction is performed in a suitable solvent which contains a salt-forming agent, below room temperature, then the solvent is distilled off and the crude distillate is fractionated.

To convert the 2-allyl-substituted perfluorocycloalkoxy- or perfluoroalkoxyperfluoropropanoic acid fluorides into 2-allyl-substituted perfluorocycloalkyl trifluorovinyl or perfluoroalkyl-trifluorovinyl ethers according to the invention, the carboxylic acid fluorides are converted into the sodium salts by alkaline saponification and these sodium salts are decarboxylated at 150° to 350° C., preferably at 180° to 240° C.

Considerable amounts of 1,1,1,2-tetrafluoroethyl compounds are produced as a side product and these have to be separated with difficulty or at great expense.

For the compounds according to the invention, a process was found for dissolving the sodium salts initially formed in aromatic hydrocarbons, preferably toluene, separating out insoluble salts and drying the sodium salts azeotropically by distillation. In this way water and alkaline impurities, which favor the appearance of the undesired 1,1,1,2-tetrafluoroethyl compounds, are largely eliminated.

Thus, the 2-allyl-substituted perfluorocycloalkyl trifluorovinyl or perfluoroalkyltrifluorovinyl ethers can be prepared with a high enough purity for polymerization trials.

Preparation of polymers according to the invention takes place via a radical route. In other respects, there are no restrictions on the method of polymerization. Polymerization may take place in bulk, solution (suitable solvents are fluoro(hydro)carbons, e.g. hexafluorocyclopentane, perfluorobutane or fluorochlorocarbons, e.g. trichlorotrifluoroethane), suspension or emulsion. Radical initiation may be promoted by energy-rich radiation, thermal energy or by radical initiators. Basically well-known compounds which are appropriate for the particular reaction medium are used for chemical initiation.

Thus, organic, oil-soluble peroxides, which may also be fluorinated, such as benzoyl peroxide, trifluoroacetyl peroxide or organic, soluble azo-compounds, such as azobisisobutyronitrile, are used for bulk, solution and suspension polymerization. In the case of emulsion polymerization, which is preferred for the preparation of copolymers according to the invention, water-soluble, inorganic per-compounds are used as initiators, such as persulphates, perborates, percarbonates, etc., generally in the form of their sodium or ammonium salts.

Depending on the polymerization temperature and on the decomposition constant of the initiator, decomposition accelerators, generally reducing agents, must also be used when using lower temperatures for polymerization. The following may be used for this purpose: sulphur compounds, such as sodium sulphite, sodium pyrosulphite or Rongalite C (sodium formamidinesulphinic acid), other organic reducing agents, such as ascorbic acid, metal salts, such as iron(II) or cobalt(II) salts, organometallic compounds, etc.

The reaction temperatures for copolymerization are between $-15$ and $+120°$ C., preferably $0°$ to $90°$ C.

The following comonomers (II) may be considered for copolymerization with the monomers (I) according to the invention:

ethylene with at least one fluorine atom (vinyl fluoride, vinylidene fluoride, trifluoroethylene, tetrafluoroethylene, trifluorochloroethylene) monomers of the $CF_2=CYX$ type, wherein $Y=H$, F or Cl and X may represent an aliphatic perfluorinated group (e.g. hexafluoropropene, hydro- or chloropentafluoropropene) or may be an $R_F$-O group (e.g. perfluoromethylperfluorovinyl ether; perfluorocyclopentyl-perfluorovinyl ether).

The copolymers may contain 1 to 99 mol-% of the monomers (I) according to the invention, depending on the properties desired. The amount of monomer (I) should be at least 20 mol-% if it is intended to be copolymerized to give an amorphous polymer with comonomers which might form polymers which are capable of crystallizing.

Copolymerization with gaseous monomers is performed under elevated pressure. This pressure should be at least 2 bar, but the value of 100 bar need not be exceeded.

EXAMPLES

Example 1 a) (2-allyl-)heptafluorocyclopentanone 750 g (3.54 mol) of octafluorocyclopentene is initially introduced at 0° to 5° C. (ice bath), 205 g (3.59 mol) of KOH powder is added and this suspension is stirred. Then 211 g (3.64 mol) of allyl alcohol is added dropwise over the course of 3 hours, the small amount of exothermic energy being trapped by the ice bath. Sniffing is continued for 16 hours at room temperature, then the mixture is stirred into 1500 ml of water and the organic phase is separated and dried over $Na_2SO_4$.

Crude yield; 785 g (3.14 mol)=88.7% of theory.

The crude material is subjected to distillation at atmospheric pressure using a 30 cm Vigreux column with a distillation head. After removal of the volatile component (octafluorocyclopentene, ca. 32 g=0.151 mol) the mixture is boiled under total reflux for 4 hours, until the sump temperature has risen to ca. 140° C. (Rearrangement of the initially formed 1-allyloxyheptafluorocyclopentene to give (2-allyl-)heptafluoro-cyclopentanone; see Tetrahedron, 23, 4243 (1967); U.S. Pat. No. 3,655,765).

Actual distillation of the product now takes place

First runnings: b.pt.$_{atm}$ up to 110° C. 67 g (GC; 63%. product, residual octafluorocyclopentene and a little allyl ether.

Main fraction: b.pt.$_{atm}$ 112° C. 615 g (2.46 mol 69.4%)

Residues: 53 g b) 2-[2-(allyl-)octafluorocyclopentoxy]perfluoropropanoic acid fluoride 150 g (2.59 mol) of ignited potassium fluoride are suspended in 500 ml of diglyme and 504 g (2.0 mol) of (2-allyl-)heptafluorocyclopentanone are added dropwise over the course of 90 minutes, with stirring and at 5° to 20° C. After the slightly exothermic reaction subsides, it is cooled to 5° C. and hexafluoropropene oxide is condensed in fast enough for only a slight reflux to occur in a dry ice condenser. After 330 g (ca. 1.99 mol) of hexafluoropropene oxide has been introduced (ca. 80 g per hour), stirring is continued overnight at room temperature.

Finally, the product and a proportion of the diglyme is distilled off under a water jet vacuum up to b.pt.$_{18\ mbar}$ ca. 50° C. Crude weight 940 g.

The coarse distillate is fractionated on a 30 cm packed column:

After a first running (102 g) of unconverted starting material, 554 g of main fraction (b.pt.$_{15\ mbar}$ 41 to 44° C.) are obtained which, according to GC, contains about 65% target product and ca. 30% diglyme.

Yield: 57.8% (with reference to the GC purity)

Ca. 15% target product, residual diglyme and multiple adducts of HFPO are left at the bottom.

$^1$H-NMR: $\delta$=2.83 ppm (dm,2H,-CH$_2$-); 5.34 ppm (dm,2H,=CH$_2$) and 5.8 ppm (m,1H,CH=) (optional internal, TMS in CDCl$_3$).

2-(allyl-)octafluorocyclopentyl-trifluorovinyl ether 554 g of distillate from Example 1b) [=ca. 360 g (1.02 mol) of 2-[2-(allyl)octafluorocyclopentoxy]-perfluoropropanoic acid fluoride]at 0° to 5° C. are initially introduced into 300 ml of dioxane, and adjusted to be alkaline against phenolphthalein using 220 g of 45% strength sodium hydroxide solution over 3 hours. A suspension is formed which is concentrated to ca. ⅓ of its volume by evaporation under a water jet vacuum. The material is stirred up with 500 ml of toluene, then insoluble salts are removed by suction and washed with toluene.

The toluene solution is concentrated in a rotary evaporator, leaving behind 553 g which is further concentrated under an oil pump vacuum at a maximum of 50° C.

The remaining 489 g of very viscous sodium salt are heated slowly to a maximum of 280° C., on a metal bath under an oil pump vacuum. The material distilled off, via a bridge, at up to 100° C. bath temperature, consists to a large extent of residual toluene and diglyme and is discarded. From 150° to 180° C., thermal decomposition of the sodium salt starts. 352 g of distillate are collected, which are fractionated on a 30 cm packed column under a water jet vacuum:

First runnings:b.pt.$_{18mbar}$ <35° C.;45g; rejected.

Fraction I b.pt.$_{18 mbar}$ 41°–48° C., 189 g, GC shows 77% target product, 15% diglyme Fraction 11 b.pt.$_{18 mbar}$ >50° C., 57 g of largely diglyme Residue ca. 50 g, crossed products.

Product fraction I is re-distilled on the same column:

Fraction I b.pt.$_{18mbar}$ 45°–47° C., 155 g, GC shows 88% target product

Residue ca. 30 g, <3% diglyme $^1$H-NNM: δ=2.79 ppm (dm,2H,—CH$_2$—); 5.30 ppm (dm,2H,=CH$_2$) and 5.72 ppm (m, 1H,CH=) (optional internal TMS in CDCl$_3$).

The 1,1,1,2-tetrafluoro-ethoxy compound occurring as an impurity gives an additional $^1$H resonance at 6.05 ppm.

Example 2 a) (2-allyl-)pentafluorocyclobutanone 320 g (1.98 mol) of hexafluorocyclobutene are condensed into 116 g (2 mol) of allyl alcohol at −5° C. Then, 113 g (1.98 mol) of KOH, dissolved in 150 ml of water, are slowly added dropwise, over the course of 3 hours, the temperature being kept at 0° to 5° C. Finally, stirring is continued overnight at room temperature.

The above is stirred into 1000 ml of water and the organic phase is separated and dried over Na$_2$SO$_4$.

Crude yield: 372 g.

The crude material is thermally rearranged, as described in Example 1a), and then fractionated at atmospheric pressure.

b.pt.$_{atm}$ 63°–65° C., 289 g (95% from GC; 1.44 mol=73%).

Residue, 75 g.

b) 2-[2-(allyl-)hexafluorocyclobutoxy]-perfluoropropanoic acid fluoride 1 mole of the ketone from Example 2a) is reacted with hexafluoropropene oxide in the same way as in Example 1b).

After working up, a product fraction (b.pt.$_{18}$ 34°–36° C.) is obtained, which is ca. 85% (GC) target compound. The yield is ca. 60%.

c) 2-(ally)-hexafluorocyclobuty]-trifluorovinyl ether

The carboxylic acid fluoride (0.5 mol, 85%) from Example 2b) is converted into a sodium salt in the same way as in example 1c) and pyrolyzed at 150°–220° C. under an oil pump vacuum. The condensate is fractionated under a water jet vacuum.

Yield: 27% with reference to the carboxylic acid fluoride used.

b.pt.$_{20 mbar}$ 32°–33° C., GC shows 82% target product.

Example 3 a) (3-allyl-)heptafluorobutan-2-one 396 g (1.98 mol) of octafluorobut-2-ene is condensed into 116 g (2 mol) of allyl alcohol at −5° C. Then 113 g (1.98 mol) of KOH, dissolved in 150 ml of water, is slowly added dropwise over the course of 3 hours, the temperature being maintained at 0°–5° C. Stirring continues overnight at room temperature and working-up is performed in the same way as in Example 2a.

Crude yield 438 g.

The crude material is thermally rearranged in the same way as in Example 1a) and then fractionated at atmospheric pressure.

b.Pt.$_{atm}$: 87°–89° C., 348 g (97% strength according to GC; 1.46 mol 73.8%)

Residue: 85 g b) 2[3-(allyl-)heptafluorobut-2-oxy]perfluoropropanoic acid fluoride 1 mole of the ketone from Example 3a) is reacted with hexafluoropropene oxide in the same way as in Example 1b).

After working-up, a product fraction (b.pt.$_{18}$ 50°–58° C.) is obtained which is about 78% target compound (from GC); the yield is about 42%.

c) 3-(allyl-)heptafluorobut-2-yl-trifluorovinyl ether

The carboxylic acid fluoride (0.5 mol, 78% strength) from Example 3b) is converted into the sodium salt in the same way as in Example 1c) and pyrolyzed under an oil pump vacuum at 150°–230° C. The condensate is fractionated under a water jet vacuum.

Yield: 29% with reference to the carboxylic acid fluoride used.

Example 4

30 g of 1,1,2,2,3,3-hexafluorocyclopentane, 50 mg of diisopropylperoxy dicarbonate and 15 g of 2-(ally-)octafluorocyclopentyl-trifluorovinyl ether (with the purity described in Example 1) were placed in a 100 ml glass flask and cooled to −50° C. with stirring. The pressure in the reaction apparatus was reduced three times to about 4 mbar and flushed out with nitrogen each time. The reaction mixture was heated to 40° C. with constant stirring. After a total reaction time of 40 hours at 40° C., the mixture was cooled down. A viscous, colorless solution with a solids content of 31.4% by weight was obtained and precipitated by stirring into ethanol. 13 g of a white, powdery polymer were isolated. The polymer is soluble in acetone. The residual amount of unconverted fluorovinyl groups, determined by $^{19}$F-NMR spectroscopy, is less than 9 mol-%, with reference to the fluorovinyl groups used (evaluated using the signal at −115 ppm in acetone-d$_6$ against CFCl$_3$ as a standard). In the $^1$H-NMR spectrum the amount of unconverted allyl groups was determined at less than 4 mol-%, with reference to the allyl groups used (evaluated using the signal at 5.3–5.5 ppm: 2 doublets and at 5.9 ppm: I sextet, measured in acetone-d$_6$).

[η]=0.031 dl/g (acetone/25° C.)

DSC: $T_g = 100°$ C.

Example 5

40 g of deionized water, 0.16 g of lithium perfluorooctylsulphonate, 0.3 g of potassium peroxydisulphate and 10 g of 2-allyl-octafluoro-cyclopentyl-trifluorovinyl ether (with the purity described in Example 1) were placed in a 100 ml glass flask and cooled to 1° C. with stirring. The pressure in the reaction apparatus was then reduced 5 times to about 20 mbar and flushed out with nitrogen each time. The reaction mixture was heated to 70° C. with constant sniffing. After a total reaction time of 10 hours at 70° C., the mixture was cooled down. After standing for several hours, about 1 g of a viscous, oily phase settled out on the base of the reaction vessel, which was separated off. 4.5 g of a white powdery polymer were isolated from the supernatant milky-white emulsion by coagulating with a 4% strength aqueous magnesium sulphate solution. The polymer is soluble in bistrifluoromethylphenol (BTFMP) and acetone without forming a gel. The limiting viscosity number is 0.042 dl/g (THF/25° C.); DSC: $T_g$ 64° C.

Example 6

Example 5 is repeated at 90° C. After a total reaction time of 4 hours, about 2 g of a viscous, oily phase settles out on the base of the reaction vessel, after cooling and standing for several hours. 3.5 g of a white powdery polymer were isolated from the supernatant milky-white emulsion by coagulating with a 4% strength aqueous magnesium sulphate solution. The polymer is soluble in bistrifluoromethylphenol (BTFMP) and acetone without forming a gel. The limiting viscosity number (Staudinger index) is 3.5 ml/g (THF/25° C.). The weight average molecular weight, determined in THF by gel chromatography, is $1.3 \times 10^4$ g/mol with a non-uniformity of 0.6 (polystyrene calibration curve). DSC: $T_g = 58°$ C.

Example 7-9

Copolymerisation of 2-allyl-octafluorocyclopentyl-trifluorovinyl ether with trifluorochloroethylene 130 ml of deionized water were initially placed in a 0.3 l autoclave. 0.5 g of lithium perfluorooctylsulphonate were dissolved therein. This solution was adjusted to a pH of about 10 using lithium hydroxide. Then nitrogen at a pressure of 10 bar was admitted to the scaled autoclave and the pressure was released to atmospheric pressure, three times in succession. The amounts given in Table 1 (=monomer 1) of 2-allyl-octafluorocyclopentyl-trifluorovinyl ether (as in Example 1) and 30 g of trifluorochloroethylene were placed in the autoclave and the reaction mixture was heated to 70° C. with stirring. After reaching this temperature, 20 g of an aqueous solution containing 0.5 g of potassium peroxydisulphate were forced into the autoclave. After the total reaction times given in Table 1, the contents of the autoclave were cooled and the unconverted mixture was evacuated. The reaction mixtures obtained in this way were poured into 130 ml of a 4% strength aqueous magnesium sulphate solution to coagulate them fully. The products were washed with water and then dried, giving copolymers (white powders) consisting of units of trifluorochloroethylene and 2-allyl-octafluorocyclopentyl-trifluorovinyl ether in the yields and compositions (using the $^{19}$F-NMR spectra or analysis of elemental chlorine), as given in Table 1.

Solubilities, limiting viscosity numbers [η] and DSC results are also listed in Table 1.

Furthermore, the polymer composition is given as the molar ratio of the polymer structural units resulting from trifluorochloroethylene to the polymer structural units resulting from 2-allyl-octafluorocylcopentyl-trifluorovinyl ether.

(1) —means that complete dissolution was not achieved +means that a gel-free solution was obtained 25 mg of polymer per ml of acetone at 25° C. were used in each case

TABLE 1

| Example | Monomer 1 | Time of polym. [hrs] | Yield of polymer [g] | Comp. of polymer (molar ratio) | [η] [dl/g] (acetone 125° C.) | $T_g$ form DSC [°C.] | Solubility (1) |
|---|---|---|---|---|---|---|---|
| 7 | 7 | 10 | 16 | 90/10 | 0.065 | 60 | — |
| 8 | 10 | 10 | 12 | 79/21 | 0.063 | 64 | + |
| 9 | 20 | 20 | 27.5 | 67/33 | 0.052 | 72 | + |

(1) — means that complete dissolution was not achieved
+ means that a gel-free solution was obtained
25 mg of polymer per ml of acetone at 25° C. were used in each case

What is claimed is:

1. A 2-allyl-perfluoroalkyl-trifluorovinyl ether of the formula

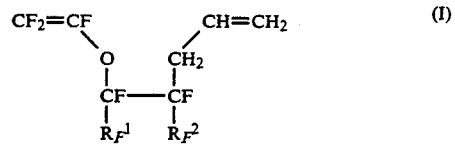

wherein $R^1_F$ and $R^2_F$ represent either —$CF_3$ or, when taken together, $(CF_2)_n$ where n=2 or 3.

2. 2-Allyl-perfluorocyclopentyl-trifluorovinyl ether according to claim 1.

* * * * *

UNITED STATES PATENT AND TRADEMARK OFFICE
CERTIFICATE OF CORRECTION

PATENT NO. : 5,313,003

DATED : May 17, 1994

INVENTOR(S) : Kruger, et al.

It is certified that error appears in the above-identified patent and that said Letters Patent is hereby corrected as shown below:

Title Page, Abstact Line 3      Delete formula (I) and substitute

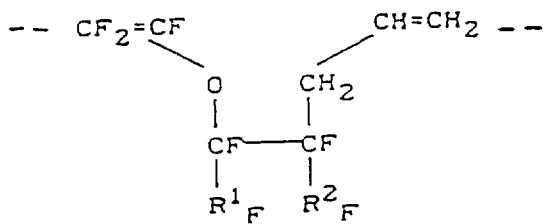

Col. 1, Line 53      Delete formula (I) and substitute

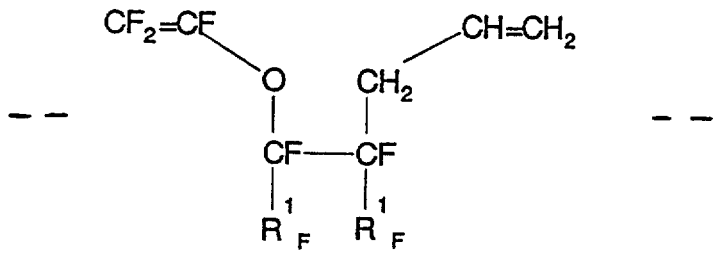

UNITED STATES PATENT AND TRADEMARK OFFICE
CERTIFICATE OF CORRECTION

PATENT NO. : 5,313,003

DATED : May 17, 1994

INVENTOR(S) : Kruger, et al.

It is certified that error appears in the above-identified patent and that said Letters Patent is hereby corrected as shown below:

Col 1., Line 53    Delete formula (I) and substitute

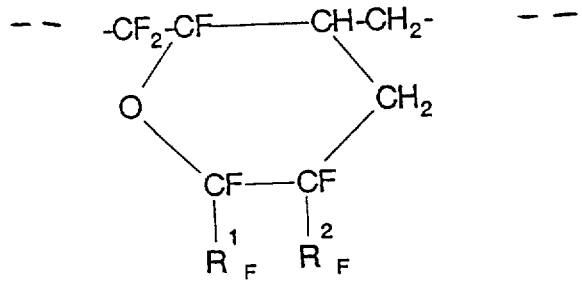

Col. 1, Line 68    Delete formula (II) and substitute

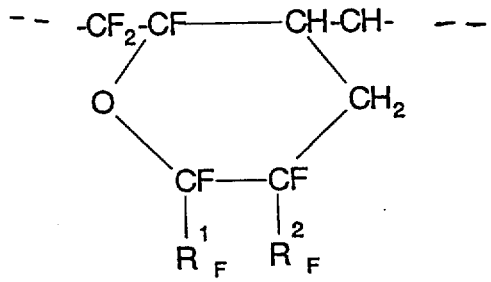

UNITED STATES PATENT AND TRADEMARK OFFICE
CERTIFICATE OF CORRECTION

PATENT NO.   : 5,313,003
DATED        : May 17, 1994
INVENTOR(S)  : Kruger, et al.

It is certified that error appears in the above-identified patent and that said Letters Patent is hereby corrected as shown below:

Col. 2, Line 13             Delete formula (IV) and substitute

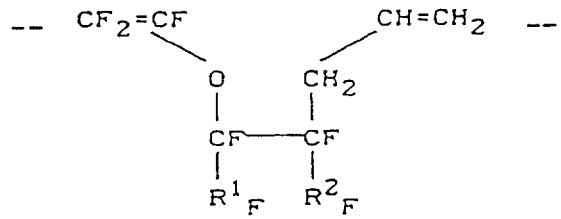

Col. 8, Line 52             Delete formula (I) and substitute

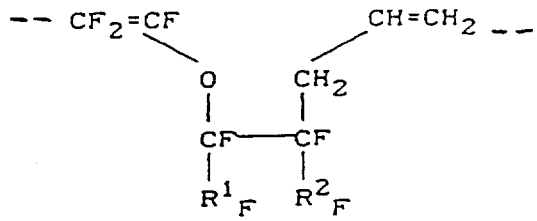

Signed and Sealed this

Fourth Day of January, 2000

Attest:

*Attesting Officer*           *Acting Commissioner of Patents and Trademarks*